US009415177B2

(12) United States Patent
Baillet et al.

(10) Patent No.: US 9,415,177 B2
(45) Date of Patent: Aug. 16, 2016

(54) DRY POWDER INHALER WITH MOVABLE PORTION TO OPEN A CAPSULE

(75) Inventors: Matthieu Baillet, Bonsecours (FR); Arnaud Colomb, Verneuil sur Seine (FR); Zakaria Sallak, Rouen (FR)

(73) Assignee: APTAR FRANCE SAS, Le Neubourg (FR)

( * ) Notice: Subject to any disclaimer, the term of this patent is extended or adjusted under 35 U.S.C. 154(b) by 659 days.

(21) Appl. No.: 13/808,482

(22) PCT Filed: Jul. 5, 2011

(86) PCT No.: PCT/FR2011/051594

§ 371 (c)(1), (2), (4) Date: Mar. 18, 2013

(87) PCT Pub. No.: WO2012/004523

PCT Pub. Date: Jan. 12, 2012

(65) Prior Publication Data

US 2013/0186398 A1 Jul. 25, 2013

(30) Foreign Application Priority Data

Jul. 7, 2010 (FR) ..................................... 10 55546

(51) Int. Cl.
*A61M 15/00* (2006.01)

(52) U.S. Cl.
CPC ....... *A61M 15/0028* (2013.01); *A61M 15/0021* (2014.02); *A61M 15/0043* (2014.02); *A61M 15/0086* (2013.01); *A61M 2202/064* (2013.01)

(58) Field of Classification Search
CPC ............ A61M 15/00; A61M 15/0005; A61M 15/0006; A61M 15/0028; A61M 15/003; A61M 15/0031; A61M 15/0043; A61M 15/0086
See application file for complete search history.

(56) References Cited

U.S. PATENT DOCUMENTS

| | | | | | |
|---|---|---|---|---|---|
| 3,669,113 | A * | 6/1972 | Altounyan | A61M 15/00 128/203.15 |
| 4,206,758 | A * | 6/1980 | Hallworth | A61M 15/0031 128/203.15 |
| 4,210,140 | A * | 7/1980 | James | A61M 15/0028 604/58 |
| 4,353,365 | A * | 10/1982 | Hallworth | A61M 15/0028 128/203.15 |
| 4,446,862 | A | 5/1984 | Baum et al. | |
| 4,846,168 | A * | 7/1989 | Abiko | A61M 15/0028 128/200.23 |
| 4,860,740 | A * | 8/1989 | Kirk | A61M 15/0028 128/203.15 |
| 5,645,051 | A * | 7/1997 | Schultz | A61M 15/0028 128/203.15 |
| 5,655,523 | A | 8/1997 | Hodson et al. | |
| 6,055,980 | A * | 5/2000 | Mecikalski | A61K 9/0075 128/203.15 |
| 2007/0151562 | A1 | 7/2007 | Jones et al. | |

FOREIGN PATENT DOCUMENTS

| | | | | |
|---|---|---|---|---|
| GB | 2064334 | A * | 6/1981 | A61M 15/0028 |
| WO | 2008/012456 | A2 | 1/2008 | |
| WO | 2009/077697 | A1 | 6/2009 | |

* cited by examiner

*Primary Examiner* — Lynne Anderson
*Assistant Examiner* — Kathryn E Ditmer
(74) *Attorney, Agent, or Firm* — Sughrue Mion, PLLC

(57) ABSTRACT

A dry-powder inhaler including a body containing a dispersion chamber; a dispenser orifice through which the user inhales; a loading opening that receives a capsule containing a dose of dry powder for inhaling; and at least one movable portion that moves relative to the body between a first end position and a second end position; the dispersion chamber containing at least a portion of an empty capsule at the moment of inhalation, the at least one capsule portion swirling in the dispersion chamber during inhalation so as to disperse and/or break up the powder.

2 Claims, 7 Drawing Sheets

DRY POWDER INHALER WITH MOVABLE PORTION TO OPEN A CAPSULE

CROSS REFERENCE TO RELATED APPLICATIONS

This application is a National Stage of International Application No. PCT/FR2011/051594, filed on Jul. 5, 2011, which claims priority from French Patent Application No. 1055546, filed on Jul. 7, 2010, the contents of all of which are incorporated herein by reference in their entirety.

The present invention relates to a dry-powder inhaler.

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Another type of inhaler consists in placing the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of metering accuracy and reproducibility on each actuation. In addition, the effectiveness of the dispensing, i.e. the fraction of the dose that effectively penetrates into the user's lungs in order to have a beneficial therapeutic effect, is also a problem that exists with a certain number of inhalers. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation. Another problem that exists with inhalers provided with blister strips is associated with the movement of the strip, and with storage of the used portion of the strip. Thus, depending on the length of the strip and/or the thickness of the blisters, a large amount of space can turn out to be necessary, and any blockage of the blister strip can prevent the inhaler from functioning properly. In addition, when the device for advancing the strip pulls simultaneously on the leading end of the strip so as to avoid poor rolling up, a problem can occur over successive actuations, in particular because the rolled-up diameter of the used strip increases progressively. Multidose inhalers and inhalers containing a blister strip are thus generally complex devices constituted by a large number of parts, and thus costly to manufacture and to assemble. In order to make devices less complex and thus less costly, inhalers have been proposed that include individual reservoirs, such as capsules, that are loaded into the inhaler just before said inhaler is used. The advantage of such devices is that it is not necessary to store all of the doses inside the appliance, such that said appliance can be compact. However, the inhaler is more difficult to use, since the user is obliged to load a capsule into the inhaler before each use. Furthermore, other drawbacks specific to such a capsule inhaler have appeared. Thus, such devices are generally constituted by two parts, one being provided with the mouthpiece. During manipulation of such devices, for opening the capsule and releasing the powder, or for ejecting the empty capsule after inhalation, the user's fingers generally come into contact with the mouthpiece, and this can present risks of contamination. In addition, in order to eject the empty capsule, the device must generally be disassembled, and this exposes the inside of the device to any external pollution, which might subsequently be transmitted to the user during a future inhalation.

An object of the present invention is to provide a dry-powder inhaler that does not have the above-mentioned drawbacks.

In particular, an object of the present invention is to provide such an inhaler that is simple and inexpensive to manufacture and to assemble, that is reliable in use, and that limits, as much as possible, the risks of contamination and/or of pollution.

The present invention thus provides a dry-powder inhaler comprising: a body containing a dispersion chamber; a dispenser orifice through which the user inhales; a loading opening that receives a capsule containing a dose of dry powder for inhaling; and at least one movable portion that moves relative to said body between a first end position and a second end position; said dispersion chamber containing at least a portion of an empty capsule at the moment of inhalation, said at least one capsule portion swirling in said dispersion chamber during inhalation so as to disperse and/or break up the powder.

Advantageously, said dispersion chamber includes air inlets that make it possible to create additional flows of air during inhalation so as to enhance the swirling of the powder in the dispersion chamber before being inhaled.

In an advantageous first embodiment, said dispersion chamber has a frustoconical shape that narrows towards the dispenser orifice so as to accelerate the inhalation flow towards said orifice.

In an advantageous second embodiment, said dispersion chamber has a shape that is substantially annular around a central axis.

These characteristics and advantages and others of the present invention appear more clearly from the following detailed description, given by way of non-limiting example, and with reference to the accompanying drawings, and in which.

Figure 13:
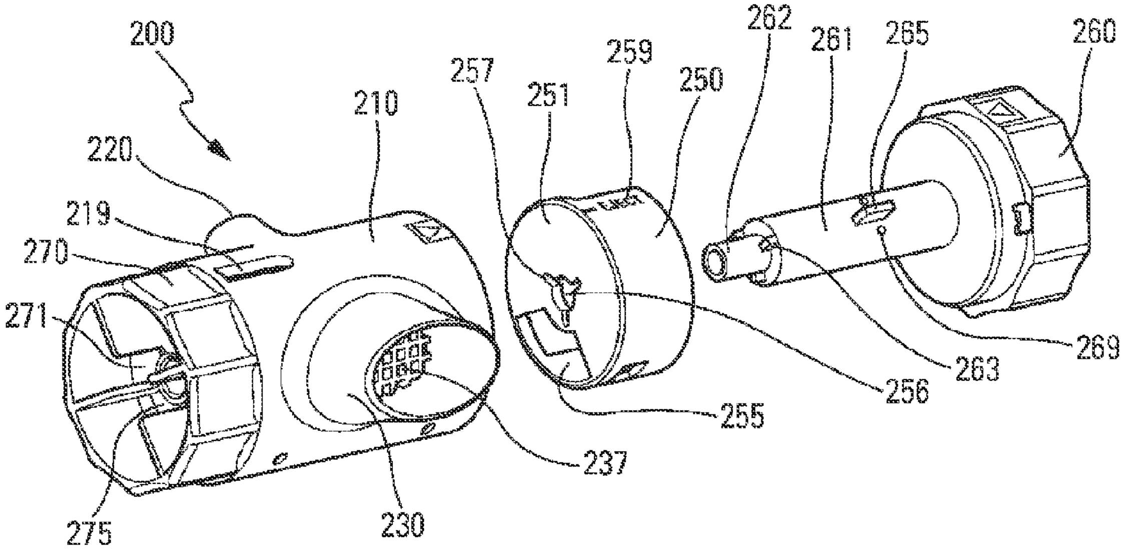
FIG. 13 is an exploded diagrammatic perspective view of a dispenser device in an advantageous second embodiment of the invention.
Figure 14A:
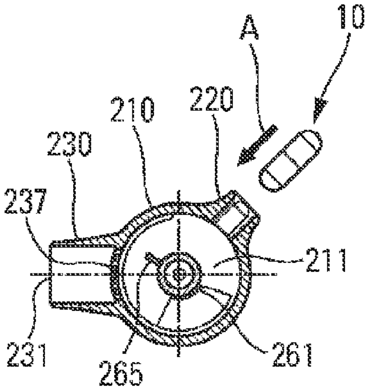
Figure 14B:
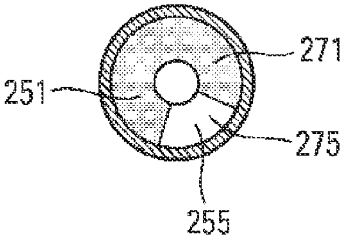

FIG. 14*a* is a diagrammatic section view of the FIG. 13 device, before the capsule has been loaded;

FIG. 14*b* is a diagrammatic view of an axial end surface of the body, showing the ejection opening formed in the position in 14*a;*

Figure 15A:
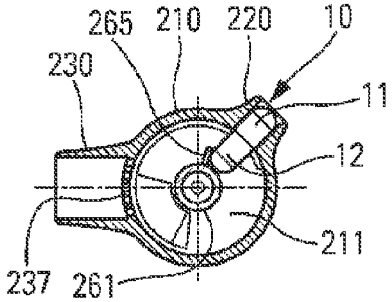
Figure 16A:
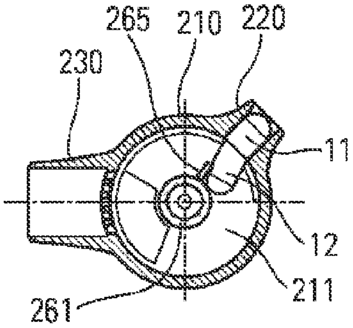
Figure 15B:
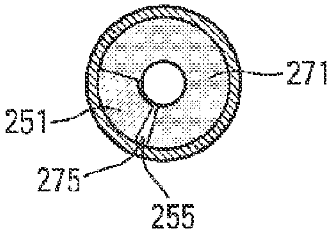
Figure 16B:
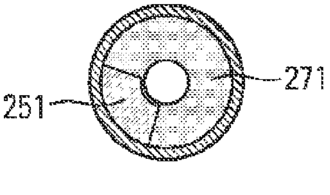
Figure 17:
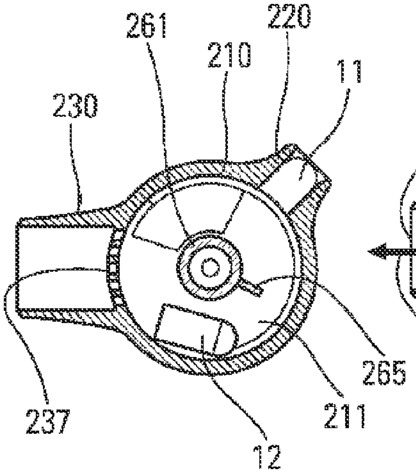
Figure 18:
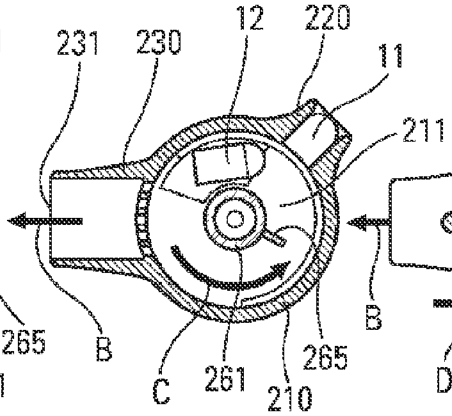
Figure 19:
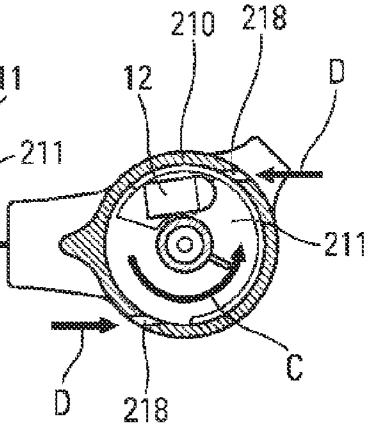
Figure 20:
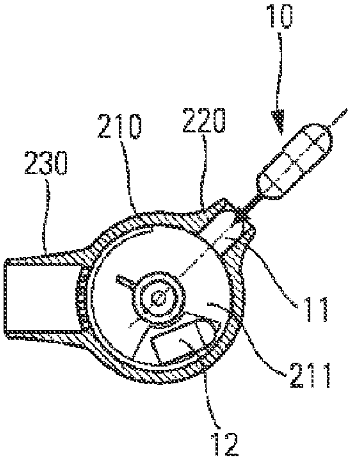
Figure 21:
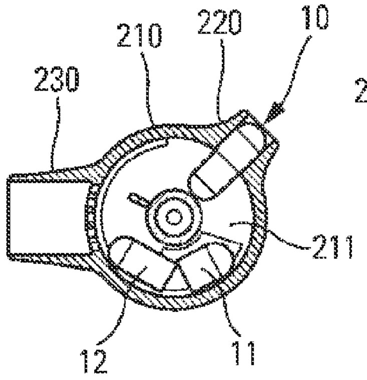
Figure 22:
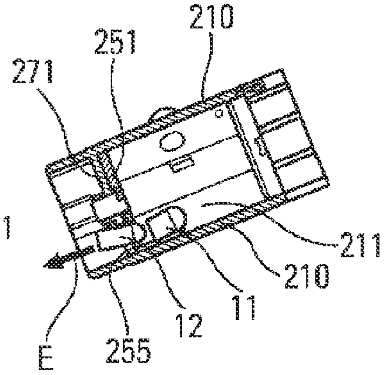

FIGS. 15*a* and 15*b* are views similar to the views in FIGS. 14*a* and 14*b*, at the start of the capsule being opened;

FIGS. 16*a* and 16*b* are views similar to the views in FIGS. 14*a* and 14*b*, during opening of the capsule;

FIG. 17 is a view similar to the view in FIG. 14*a*, after the capsule has been opened and before inhalation;

FIG. 18 is a view similar to the view in FIG. 17, during inhalation;

FIG. 19 is a view similar to the view in FIG. 18, on another section line;

FIG. 20 is a view similar to the view in FIG. 18, after inhalation and before the next capsule has been loaded;

FIG. 21 is a view similar to the view in FIG. 20, after the next capsule has been loaded; and FIG. 22 is a diagrammatic view on another cross-section of the FIG. 13 device, showing the capsule being ejected into the position in FIG. 21.

Figure 1:
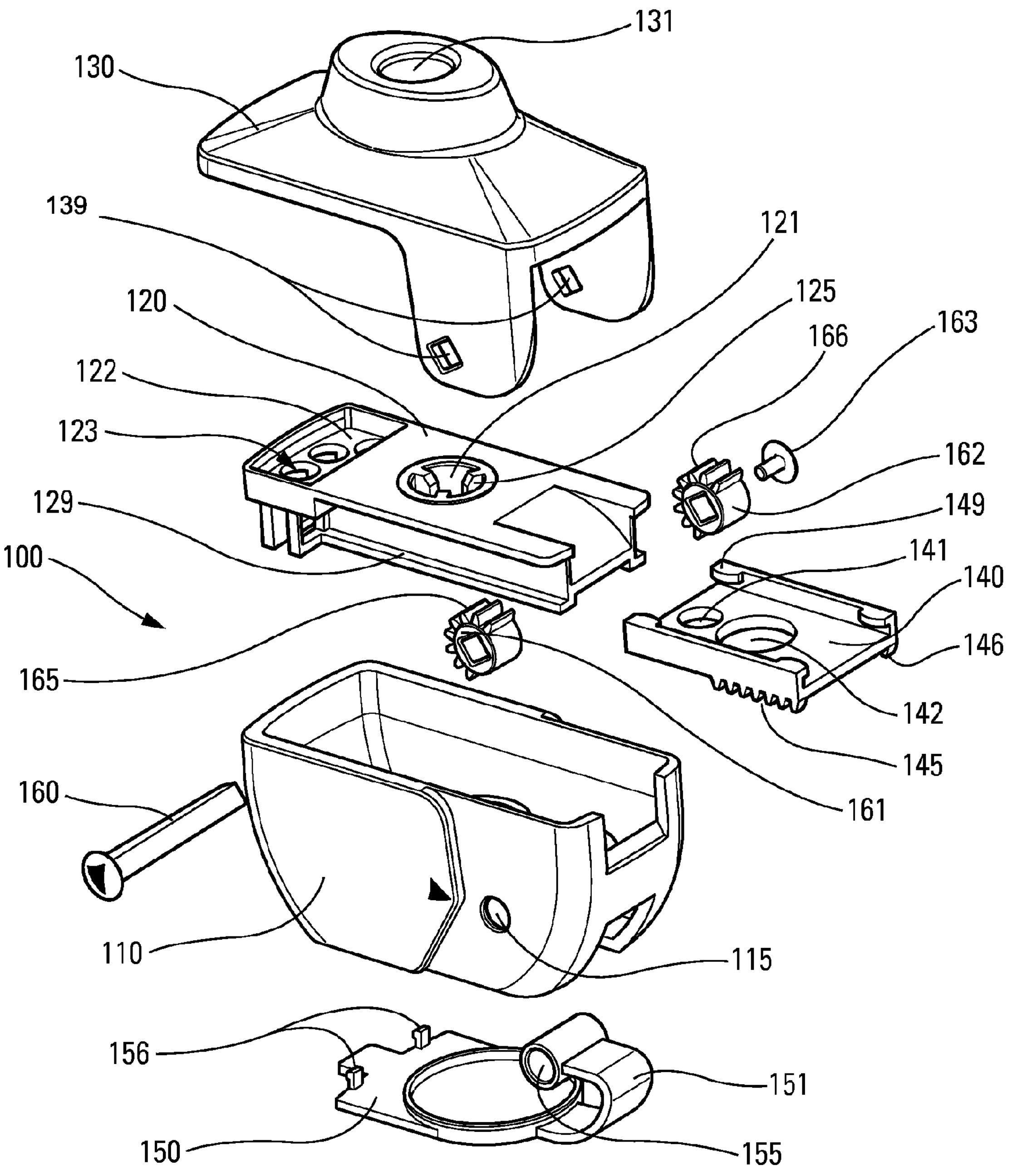
FIG. 1 is an exploded diagrammatic perspective view of a dispenser device in an advantageous first embodiment of the invention.

FIGS. 1 to 12 show a first embodiment of the invention. In this first embodiment, the inhaler 100 includes a body 110 that is hollow and that has a top opening and a bottom opening. The top opening is closed, at least in part, by a plate portion 120 that is fastened on said body, and the bottom opening is closed by a closure element, such as a shutter 150, that is pivotably mounted on said body 110. Below the plate portion 120 there is interposed a slidable member 140 that is provided with a set of teeth. Advantageously, the plate portion 120 includes guide means, such as rails 129, that co-operate with projections 149 of the slidable member 140, so as to guide the movement in translation of said slidable member. A pivotable cap 130 is assembled above said plate portion 120. The cap 130 includes the dispenser orifice 131, preferably formed at a mouthpiece around which the user places the mouth so as to inhale. Thus, as can be seen in particular in FIG. 1, the device in this first embodiment is constituted by five main parts, namely the body 110, the plate portion 120, the slidable member 140, the cap 130, and the shutter 150. All of the elements are assembled together by means of a pin 160 that passes through a side opening 115 provided in the body 110, through appropriate side openings 139 of the cap 130, and through a hollow cylinder 155 formed in a portion of the shutter 150. At least one toothed element 161, 162 is mounted on said pin 160 so as to co-operate with at least one set of teeth 145 provided on the slidable member 140. In the embodiment shown, there are two toothed elements 161 and 162 mounted on the pin 160, and thus slidable member 140 also includes two sets of teeth 145 and 146, the operation of which is described below. An appropriate fastener member 163 may be provided for fastening said pin 160 in irremovable manner on said body 110, assembling the various component parts together. As can be seen in FIG. 1, the pin 160 preferably has a particular section, e.g. substantially square, and the toothed elements also have a similar section so that they are constrained to turn with the pin 160. In addition, the cap 130 also includes openings 139 of similar shape so that the cap, the toothed elements, and said pin 160 are constrained to turn together. The plate portion 120 includes a loading opening 121, advantageously provided with at least one, and preferably three, positioning splines 125, advantageously distributed regularly around said loading opening 121. The splines make it possible to position a capsule 10 in the desired position and to hold it tightly. In particular, the capsules 10 comprise a top portion 11, and a bottom portion 12 that is separable from said top portion, said splines 125 serve to hold said top portion 11 before and during separation of said bottom portion 12. In addition, the plate portion 120 also advantageously includes a reservoir zone 122 that is formed by a zone provided with a plurality of holes 123, making it possible to have one or more capsules in reserve. This enables the user to have several capsules available at all times, e.g. while travelling. In this configuration, after each use of the device, the user has only to access the capsule reservoir in order to load the next capsule in the loading opening 121. Naturally, such a capsule reservoir is not essential to the operation of the device.

Figure 2:
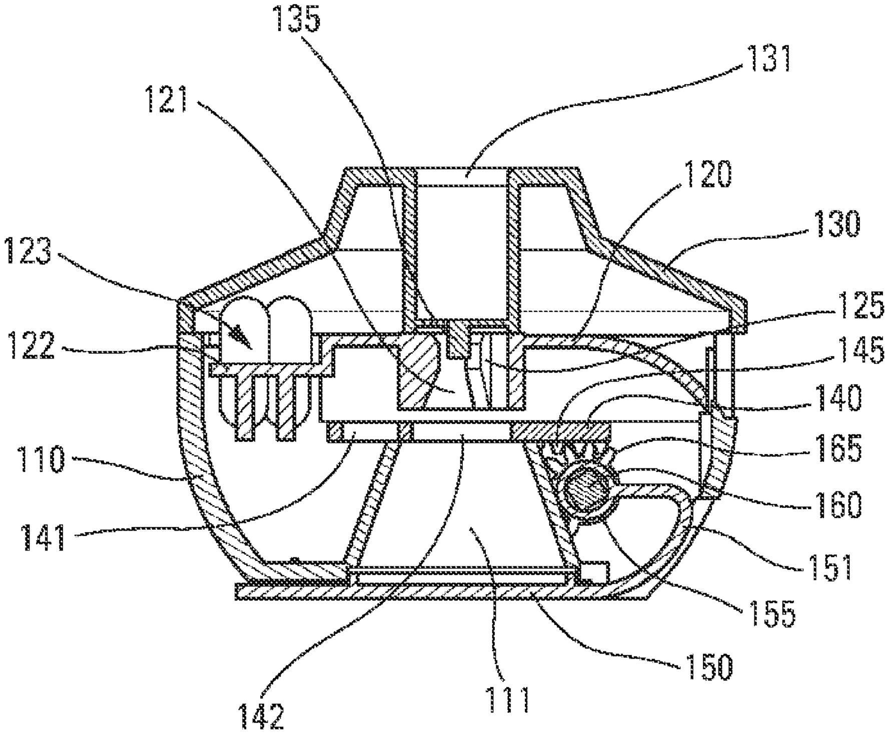
FIG. 2 is a diagrammatic section view of the FIG. 1 device, in its closed position before first use.
Figure 3:
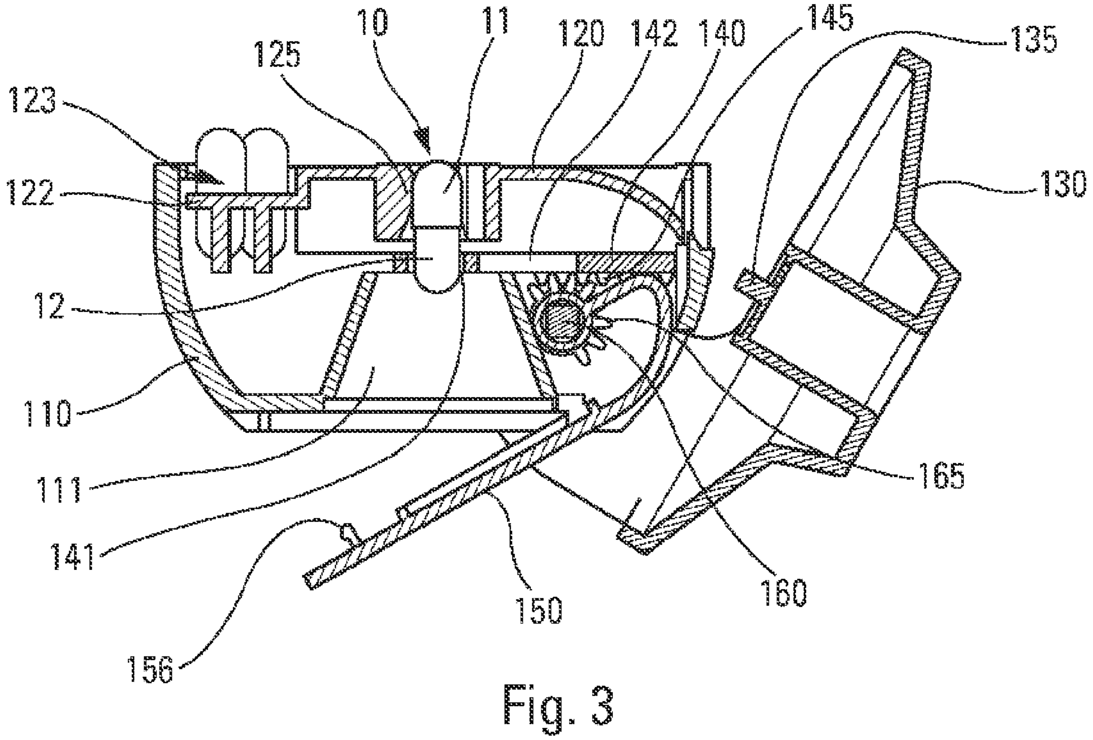
FIG. 3 is a view similar to the view in FIG. 2, in the open position, with a capsule loaded in the loading opening.

FIGS. 2 to 8 show an operating cycle of the device in this first embodiment. With reference to FIG. 2, which shows the device in its closed position before first use, it should be observed that the body 110 internally defines a dispersion chamber 111 that is for receiving the powder after the capsule 10 has been opened. FIG. 3 shows the device after the cap 130 has been opened. It should be observed that opening the cap 130 causes the pin 160 to turn, as a result of the approximately square shape of the pin 160 co-operating with the correspondingly-shaped orifices 139 of said cap 130. The turning of the pin 160 thus also causes turning of the toothed elements 161 and 162 which turn with said pin 160. The turning of the toothed elements 161, 162 causes the slidable member 140 to move sideways in translation. As shown in particular in FIG. 2, the set of teeth 165 of the toothed element 161 mesh with the set of teeth 145 of the slidable member 140. Thus, between FIGS. 2 and 3, it should be observed that turning the set of teeth 165 of the toothed element causes the slidable member 140 to slide to the right in the figures. Naturally, the same thing occurs on the other side of the device with the second toothed element 162, not shown in section in the figures. Naturally, a single toothed-element may be sufficient to cause said slidable member to move. While the cap 130 is opening, the shutter 150 does not turn with the pin 160. However, at the end of opening of the cap 130, said cap co-operates with said shutter 150 and, in particular, with a curved portion 151 that connects the hollow cylinder 155, that is mounted on the pin 160, to the portion of the shutter that closes the bottom of the body 110 in the closed position of the shutter. This co-operation between the cap 130 and the shutter 150 causes the shutter to pivot about said pin 160 towards the open position shown in FIG. 3. Thus, in this completely open position of the cap 130, the shutter 150 is open and the contents of the dispersion chamber 111 may be ejected from the device. FIG. 3 also shows a capsule 10 put into place inside the loading opening 121. It should be observed that the top portion 11 of the capsule is held tightly in the splines 125 provided in said loading opening 121. In addition, the bottom portion 12 of the capsule passes through a first opening 141 that is formed in said slidable member 140 and that, in the open position of the cap 130, is situated facing said loading opening 121.

Figure 4:
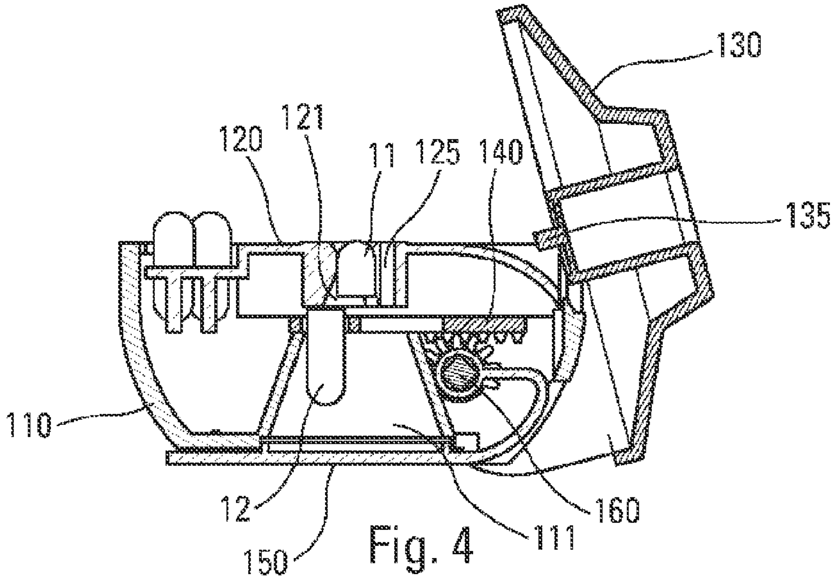
FIGS. 4 and 5 are views similar to the view in FIG. 2, during closure of the cap and opening of the capsule.
Figure 5:
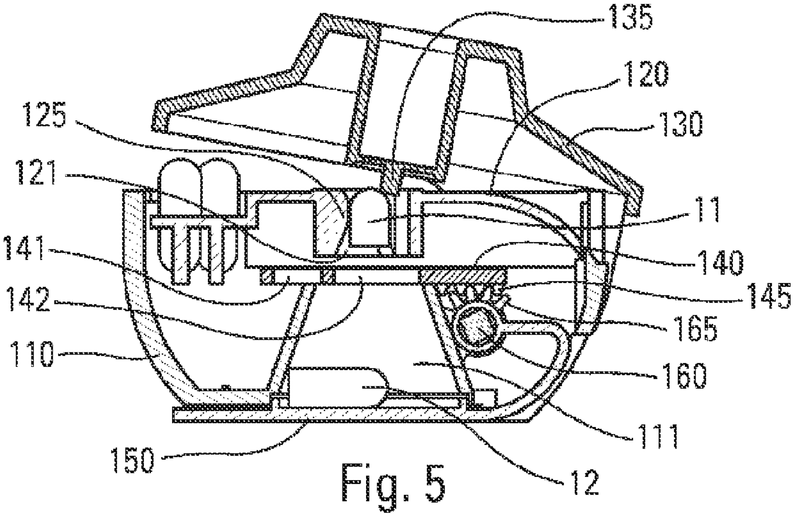
Figure 6:
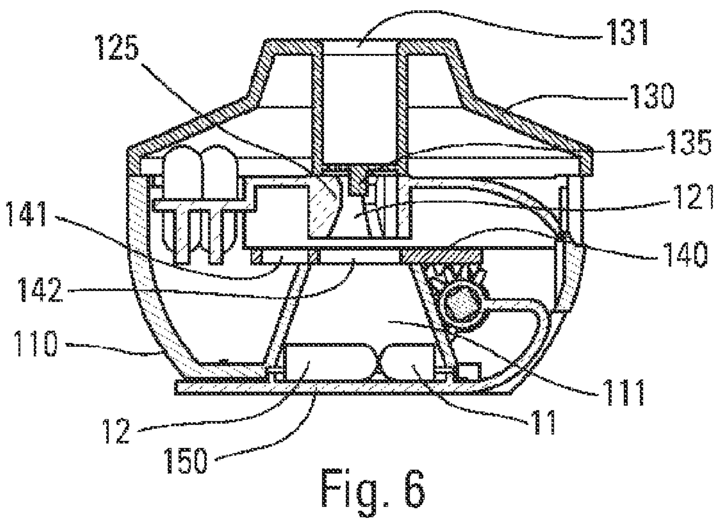
FIG. 6 is a view similar to the view in FIG. 2, in the closed position, before inhalation.

FIGS. 4 to 6 show the stage of closing the cap 130 after loading the capsule 10. Thus, as can be seen in FIG. 4, when the user closes the cap 130, the shutter 150 also closes and the slidable member 140 returns to the left in the figures by co-operation between the toothed elements 161 and 162 and the sets of teeth of said slidable member 140. However, since the bottom portion 12 of the capsule 10 passes through the first opening 141 of said slidable member 140, a sideways movement of the slidable member breaks the bottom portion 12 of the capsule 10, as shown in FIG. 4. The top portion 11 of the capsule 10 naturally remains held tightly in the loading opening 121, in particular by the splines 125. However, the bottom portion 12 falls into the dispersion chamber 111, since the first orifice 141 of said slidable member 140 has a diameter that is wider than the outside diameter of said bottom portion 12 of the capsule. Thus, not only is the powder emptied into the dispersion chamber 111, but the bottom portion 12 containing said powder falls onto the bottom wall of said dispersion chamber 111, so as to enable said bottom portion to empty. In the position in FIG. 5, it should be observed that the cap 130 is just before its closed position. In this position, a lug 135, provided in said cap portion 130, co-operates with the top portion 11 of the capsule 10 that remains in the loading opening 121. Thus, and as shown clearly in FIGS. 5 and 6, while the cap 130 is being closed completely, the lug 135 causes the top portion 11 of the capsule to be ejected from the loading opening 121 into the dispersion chamber 111. In this position, in FIG. 6, in which the device is once again closed completely, the capsule 10 is broken in two, the top and bottom portions 11 and 12 of the capsule 10 lying in the dispersion chamber 111 on the bottom wall (formed by the shutter 150), and with the powder expelled from said capsule portions, at least in part. The device is thus ready for inhalation.

Figure 7:
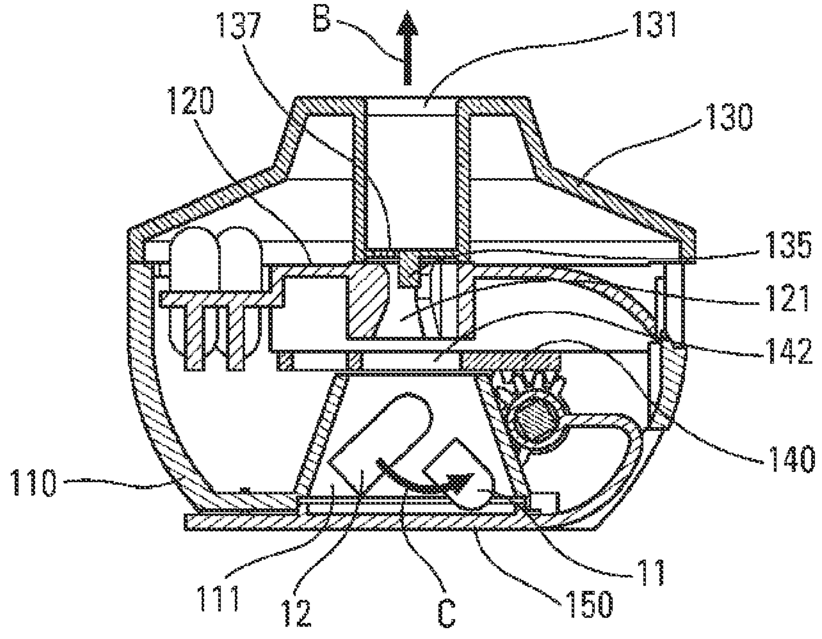
FIG. 7 is a view similar to the view in FIG. 6, in the closed position, during inhalation.
Figure 8:
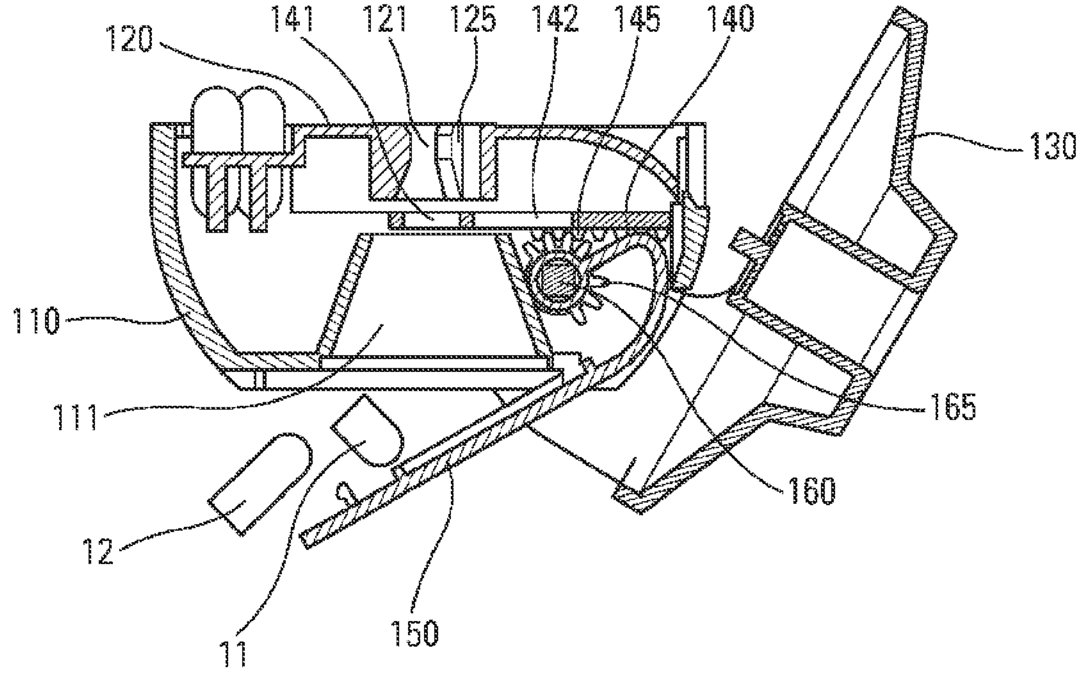
FIG. 8 is a view similar to the views in FIG. 3, in the open position.

FIG. 7 shows the inhalation stage. In order to inhale, the user places the mouth around the dispenser orifice 131 of the cap 130 and sucks in the direction of arrow B, shown in FIG. 7. In this way, a stream of air is created inside the dispersion chamber 111 that causes the two capsule portions 11 and 12 to swirl inside said dispersion chamber 111. The swirling, represented by arrow C in FIG. 7, enables said capsule portions to empty completely, and also enables the powder to be properly dispersed, and in particular enables lumps of powder that might possibly have formed to be broken up. Optionally, additional air inlets may be provided in the dispersion chamber so as to encourage the inhalation flow to swirl. The powder that swirls is then expelled from the dispersion chamber 111 by the inhalation flow, and through a second opening 142 that is provided in the slidable member 140 and that, in this inhalation position, is situated facing firstly the dispersion chamber 111 and secondly the loading opening 121. As can be seen more clearly in FIG. 11, the cap 130 advantageously includes a grid 137 through which the powder can pass and be expelled towards the dispenser orifice 131. In particular, the grid avoids the capsule portions 11, 12 also being expelled from the dispersion chamber. The user thus inhales the dose of powder that was initially contained in the capsule 10. Advantageously, said dispersion chamber may have a frustoconical shape that narrows towards the dispenser orifice 131, in particular so as to accelerate the inhalation flow towards said orifice.

After inhalation, the user once again opens the cap 130 which, as before, causes the shutter 150 to pivot at the end of opening. This pivoting of the shutter 150, shown in FIG. 8, makes it possible to eject the two empty capsule portions 11 and 12 from the dispersion chamber 111. In this position, in FIG. 8, the device is thus ready for using again. Naturally, if it is not used again immediately, the user may close the device and not re-open it until the next time that it is needed. In a variant, the user is not obliged to eject the empty capsule portions after each inhalation, but naturally may merely do that the next time the device is opened, when the user wishes to load a new capsule.

Figure 11:
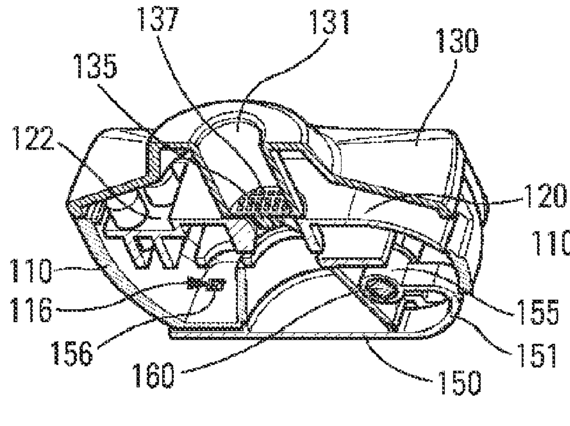
FIGS. 11 and 12 are cut-away diagrammatic perspective views, in the closed and open positions respectively.
Figure 12:
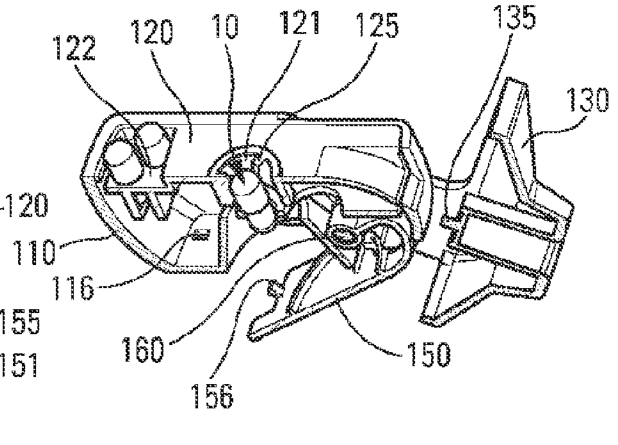

Advantageously, as shown in particular in FIG. 1, the shutter 150 may include one or more fastener lugs 156 that snap-fasten easily into the bottom wall of the body 110 in the closed position, so as to guarantee safe and reliable closure of the shutter 150 in the closed position. FIGS. 11 and 12 show openings 116 formed in the bottom wall of the body 110 through which said snap-fastener lugs 156 of the shutter can pass. Naturally, the snap-fastening does not fasten too strongly, so as to avoid hindering opening of the shutter when the user opens the cap 130.

Figure 9:
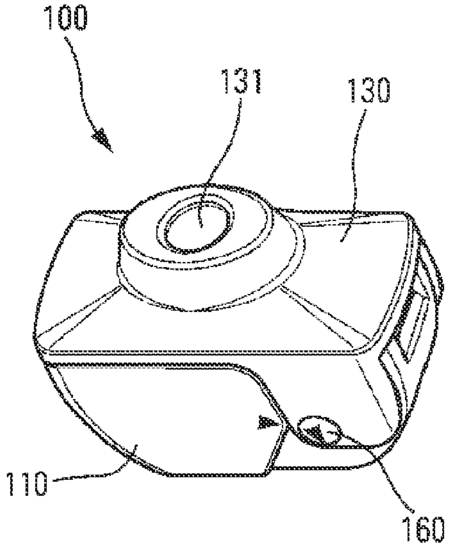
FIGS. 9 and 10 are diagrammatic perspective views of the FIG. 1 device, in the closed and open positions respectively.
Figure 10:
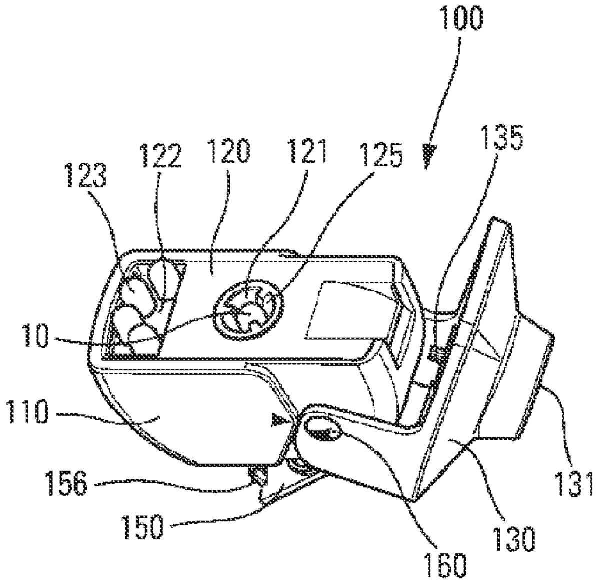

FIGS. 9 and 10 are perspective views of the device in the closed and open positions respectively, and FIGS. 11 and 12 are views similar to FIGS. 9 and 10, but cut away in part, showing the internal structure of the device in both positions.

The device of the invention is thus particularly simple and ingenious. It is made up of a small number of parts and is thus inexpensive to manufacture and to assemble. In addition, the presence of a dispersion chamber and of empty capsule portions that swirl makes it possible to break up the powder and thus guarantee that said powder is dispensed better to the user during inhalation. Finally, the ejection of the empty capsule portions does not require the device to be disassembled, and this limits the risks of said device being polluted. Not disassembling the device also avoids the risks of no longer being able to reassemble it, or of misplacing the disassembled parts, in particular for children or elderly people. Furthermore, manipulating the device, i.e. opening and closing the cap 130, does not require manipulation of the portion forming the mouthpiece around the dispenser orifice 131. Optionally, it is possible to envisage a specific grip portion for manipulating said cap. The risks of contamination at the dispenser orifice 131 are thus also limited. The method of using the device is thus very simple, the user having only to move the cap between its two end positions in order to actuate the device completely. Thus, the user firstly opens the cap, then inserts a capsule, and then closes the cap and inhales.

FIGS. 13 to 22 show a second embodiment of the present invention. In particular, FIG. 13 is an exploded perspective view of the device. In this second embodiment, the inhaler 200 is constituted by only three parts. A body 210 of shape that is substantially cylindrical is provided on its periphery with a mouthpiece 230 that defines the dispenser orifice, and with a loading opening 220 that is adapted to receive a capsule 10. The body 210 includes a longitudinal central pin, and the inside of the cylinder 210 defines a dispersion chamber 211. A first axial end portion of said body 210 is formed by a first grip portion 270 that is stationary relative to the body 210. The first grip portion could be formed merely by an axial edge of said body. Advantageously, as shown, the first grip portion 270 presents a particular outer profile, so as to encourage the user to manipulate the device by means of said grip portion. The first grip portion 270 includes a closure wall 271 for closing the dispersion chamber 211, said closure wall 271 having an opening 275, e.g. extending over an angle in the range about 60° to 90° in said closure wall 271. At the other end, the body 210 is open, and the opening is closed by a second grip portion 260 that is mounted to turn relative to said body 210. The second grip portion 260 thus forms the second axial end portion of the body. Advantageously, the second grip portion 260 presents and outer profile that is similar to the outer profile of the first grip portion 270. The user is thus naturally encouraged to take hold of each grip portion 260, 270 with a respective hand, and to turn one portion relative to the other so as to manipulate the device. Inside the cylindrical body 210, beside the first axial end portion, there is arranged a closure element, such as a shutter member 250, that also includes an axial wall 251 provided with a window 255 having dimensions that correspond approximately to the window 275 formed in the closure wall 271 of the body 210. The shutter member 250 is mounted on, and constrained to turn with, a central pin 261 that is connected to said second grip portion 260. By way of example, ribs 263 formed on the end 262 of the central pin 261 co-operate with grooves 257 of said shutter member 250, as shown in FIG. 13. The shutter member 250 is thus constrained to turn with the second grip portion 260 of the device. The shutter member 250 is arranged inside the body 210 so as to co-operate with the closure wall 271 thereof. Thus, in order to use the device of this second embodiment, the user grips the two grip portions 260 and 270 with two hands, and turns one portion relative to the other, as explained in greater detail below. At no moment is the user required to touch the mouthpiece portion 230 in order to user the device.

FIGS. 14*a*, 15*a*, and 16*a* show a stage of loading and of opening a capsule 10. Thus, with reference more particularly to FIG. 14*a*, there can be seen a cross-section through the body 210, and thus the dispersion chamber 211, the loading opening 220, and the mouthpiece 230, with, at the center, the central pin 261 that is mounted to turn in said dispersion chamber 211. The user loads a capsule 10 along arrow A into the loading opening 220. The depth of said orifice 220 is arranged so that when the user inserts the capsule 10 fully into said loading opening 220, the top portion 11 of the capsule is held tightly in said loading opening 220, while the bottom portion 12 of the capsule projects into the dispersion chamber 211. The user then turns the second grip portion 260 relative to the first 270, and thus relative to the body 210. Such turning is shown in FIGS. 15*a* and 16*a*. as can be seen in particular in FIG. 13, the central pin 261 is provided with a projection 265, e.g. in the shape of a tab. As can be seen in FIGS. 15*a* and 16*a*, while the second grip portion 260 is being turned relative to the body 210, said projection 265 comes into contact with the bottom portion 12 of the capsule. FIG. 15*a* shows the position just before the capsule is opened, while FIG. 16*a* shows the capsule during opening, with the projection 265 pushing against the bottom portion 12 of the capsule. It can be seen that turning the first pin 261 causes the projection 265 to turn, which projection deforms the bottom capsule portion that thus separates from the top capsule portion 11, which remains jammed in the loading opening 220. FIG. 17 shows the position of the open capsule 10, with the top portion 11 jammed in the loading opening 220, and the bottom portion 12 that has fallen freely into the dispersion chamber 211 so as to empty therein. FIGS. 14*b*, 15*b*, and 16*b* show what happens at the first axial end portion of the body, and in particular at the closure wall 271 of the dispersion chamber. Thus, in the position in FIG. 14*a*, at the moment of loading the capsule 10, the window 255 of the axial wall 251 of the shutter member 250 is facing the window 275 of the closure wall 271. When the user turns the second grip portion 260, the shutter member 250 also turns since said shutter member is constrained to turn with the handling element 260. The wall portion 251 thus progressively closes the opening 275 of the axial closure wall 271 of the body 210. FIG. 15*b* shows that just before the capsule starts to be opened, there is still a small open passage, but as soon as the capsule is deformed, the opening is completely closed, as shown in FIG. 16*b*, and the inside of the dispersion chamber 211 is thus closed. Thus, when the capsule breaks and the powder empties into the dispersion chamber 211, said dispersion chamber is closed at its axial end walls.

The user may then inhale, as represented by arrow B in FIG. 18. To do this, the user places the mouth around the mouthpiece and creates an inhalation flow that makes it possible to inhale the powder contained in the dispersion chamber 211, through the dispenser orifice 231. The substantially annular shape of the dispersion chamber 211 around the central axis 261 is advantageous in that it promotes the swirling of the inhalation flow coming from the mouthpiece. As in the first embodiment, the mouthpiece preferably includes a grid 237 so as to allow the powder to pass, but prevent the capsule portions from being expelled into the mouth of the user. The inhalation flow created by the user swirls the bottom capsule portion 12 that turns freely inside the dispersion chamber. Once again, this ensures that said bottom capsule portion is emptied, and enables the powder to be properly dispersed and broken up when dispensed to the user. The swirling is represented by arrow C in FIG. 18. As can be seen in FIG. 19, which shows the device on a section line that is slightly offset, it should be observed that the dispersion chamber 211 has one or more tangential openings 218 formed in the body 210. This promotes the swirling of the inhalation flow since the user, on inhalation, sucks flows of air through the tangential openings 218 (arrows D), which flows of air naturally thus turn inside said dispersion chamber 211, and thus swirl the bottom capsule portion 12 even more, so as to disperse and break up the powder.

Advantageously, the central pin 261 has openings 269, e.g. arranged around the projection 265. This is shown in FIG. 13, but other openings 269 could also be provided along the pin 261. The openings have two effects. Firstly, they enable additional air to be admitted during inhalation, and thus create different flows that further promote the emptying of the capsule, swirling, and the break-up of the powder. Secondly, the holes arranged in the proximity of the projection 265 guarantee that the bottom capsule portion 12 does not become engaged on said projection 265, trapping powder therein. As soon as the user inhales, the flow of air that passes through said orifices 269 ejects said capsule portion even if it had become engaged on said projection 265.

After inhalation, the user preferably returns the device to its start position, by turning the second grip portion 260 in the opposite direction relative to the body. In this way, the user once again opens the window 275 of the axial closure wall 271, and thus enables the bottom capsule portion 12 to be ejected through the aligned windows 255 and 275. When the user loads the next capsule 10 into the loading opening 220, as shown in FIG. 20, the top portion 11 of the previous capsule, that remained jammed in the loading opening 220, is pushed into the dispersion chamber 211. Said top portion can thus also be ejected from the dispersion chamber. This is shown in FIGS. 21 and 22. In this position in which the windows 255 and 275 are facing each other, the user may merely slope the device and eject the capsule portion(s) through said windows. Advantageously, in order to encourage the user to load the next capsule in the first position, namely the position in which the dispersion chamber is open, the body 210 includes a window 219, and the shutter member 250 includes an indicator 259, e.g. the word EJECT, that comes to be displayed in said window 219 when the two windows 255, 275 are facing each other. Optionally, in the second end position, i.e. in the position in which the capsule has been opened, the word INHALE or similar could be displayed in the window 219 so as to indicate to the user that the inhaler is in the position in which the user may inhale. Visual markers may also be provided on the second grip portion 260 and/or the body 210, so as to indicate visually to the user the two end positions of said second grip portion relative to said body.

This second embodiment of the present invention thus enables a device to be made in which the user does not need to manipulate the mouthpiece in order to use the device. Furthermore, the user also does not need to disassemble the device in order to expel or eject the empty capsule portions after each use. The risks of contamination and of pollution and thus greatly limited, as well as the risk of losing disassembled component parts, or the risk of no longer being able to assemble the device after disassembly. This second embodiment is even simpler than the first, since it comprises only three parts. It makes it possible to guarantee that the powder is properly dispersed, firstly by breaking it up in appropriate manner by means of the capsule portion that swirls in the dispersion chamber, but also by means of additional air inlets formed in the body 210 and/or in the central pin 261. The method of using the device is also very simple, the user having only to move the second grip portion between its two end positions in order to actuate the device completely. Thus, the user firstly inserts a capsule, then turns the second grip portion towards its second end position, then inhales, and then returns the grip portion towards its first end position.

Various modifications may also be envisaged by a person skilled in the art, without going beyond the ambit of the present invention, as defined by the accompanying claims. In particular, the various characteristics and functions of the device described with reference to the drawings can be combined together in any appropriate manner.

The invention claimed is:

1. A dry-powder inhaler comprising: a body containing a dispersion chamber; a dispenser orifice through which the user inhales; a loading opening that receives a capsule formed of two portions and containing a dose of dry powder for inhaling; and at least one movable portion that moves relative to said body between a first end position and a second end position; the inhaler configured such that, while moving between the first end position and the second end position, said movable portion actuates a rotary projection that is adapted to open said capsule by separating said two capsule portions from each other, such that said dispersion chamber contains at least a portion of an empty capsule at the moment of inhalation, said at least one capsule portion swirling in said dispersion chamber during inhalation so as to disperse and/or break up the powder; and wherein said at least one movable portion comprises a central pin, wherein said central pin comprises said rotary projection, and wherein said dispersion chamber has a shape that is substantially annular around a central pin.

2. The inhaler according to claim 1, wherein, said dispersion chamber includes air inlets that create additional flow of air during inhalation so as to enhance the swirling of the powder in the dispersion chamber before being inhaled.

* * * * *